United States Patent [19]

Lawless et al.

[11] Patent Number: 5,000,664

[45] Date of Patent: Mar. 19, 1991

[54] APPARATUS AND METHOD TO TEST FOR VALVE LEAKAGE IN A PUMP ASSEMBLY

[75] Inventors: Michael W. Lawless, Boulder Creek; Walter L. Jimison, Palo Alto; Giovanni Pastrone, Los Gatos; Anthony C. Yung, Milpitas, all of Calif.

[73] Assignee: Abbott Laboratories, Abbott Park, Ill.

[21] Appl. No.: 362,888

[22] Filed: Jun. 7, 1989

[51] Int. Cl.$^5$ .............................................. F04B 51/00
[52] U.S. Cl. ........................................ 417/63; 73/168
[58] Field of Search ................. 417/9, 63, 479; 73/40, 73/46, 168

[56] References Cited

U.S. PATENT DOCUMENTS

| | | | |
|---|---|---|---|
| 2,098,677 | 11/1937 | Saballus et al. | 73/168 X |
| 4,155,362 | 5/1979 | Jess | 128/214 F |
| 4,181,017 | 1/1980 | Markle | 73/168 |
| 4,278,085 | 7/1981 | Shim | 128/214 F |
| 4,341,116 | 7/1982 | Bilstad et al. | 73/290 V |
| 4,394,862 | 7/1983 | Shim | 604/67 |
| 4,460,355 | 7/1984 | Layman | 604/118 |
| 4,470,758 | 9/1984 | Pazemenas et al. | 417/63 |
| 4,479,761 | 10/1984 | Bilstad et al. | 417/479 X |
| 4,501,531 | 2/1985 | Bilstad et al. | 417/63 |
| 4,549,853 | 10/1985 | Gasper et al. | 417/63 X |
| 4,553,958 | 11/1985 | LeCocq | 604/67 |
| 4,657,490 | 4/1987 | Abbott | 417/478 |
| 4,747,826 | 5/1988 | Sassano | 604/52 |
| 4,752,289 | 6/1988 | Balding et al. | 604/118 |
| 4,758,228 | 7/1988 | Williams | 604/153 |
| 4,818,186 | 4/1989 | Pastrone et al. | 417/63 |
| 4,840,542 | 6/1989 | Abbot | 417/9 |

Primary Examiner—John C. Fox

Attorney, Agent, or Firm—Christensen, O'Connor, Johnson & Kindness

[57] ABSTRACT

Apparatus and method for determining leakage, particularly of valves, in a pumping cassette. A cassette (70) includes a primary valve (34) and a secondary valve (36), which may be selectively activated to control the source of fluid input to the cassette. The cassette also includes an inlet valve (48) and an outlet valve (56) disposed on each side of a pumping chamber (52). Downstream of the outlet valve is disposed a pressure sensor (60) which produces a signal indicative of the pressure of fluid within the cassette at that point. The cassette also includes an air-in-line sensor (40), disposed between a manifold line (38) that connects the primary and secondary valve in fluid communication with an air trap reservoir (44). Leakage in the inlet or outlet valves is detected by closing both valves, pressurizing fluid in the pumping chamber for a predetermined period of time, and then opening the outlet valve. If a pressure pulse having an amplitude less than a predetermined level is detected downstream of the outlet valve when it is opened, either the inlet or outlet valve has leaked. The primary and secondary valves are checked for leakage either by pressurizing fluid in the pumping chamber and checking for retrograde flow of air trapped in the air trap reservoir through the air-in-line sensor, or by pressurizing fluid trapped in the cassette, holding the pressure for a period of time before closing the inlet valve, and then opening the outlet valve to detect a pressure pulse propagating downstream of the outlet valve, using the pressure sensor. If a pressure pulse of less than the predetermined magnitude is detected, one of the primary or secondary outlet valves is leaking. Both tests also detect leakage of other portions of the pumping cassette.

27 Claims, 10 Drawing Sheets

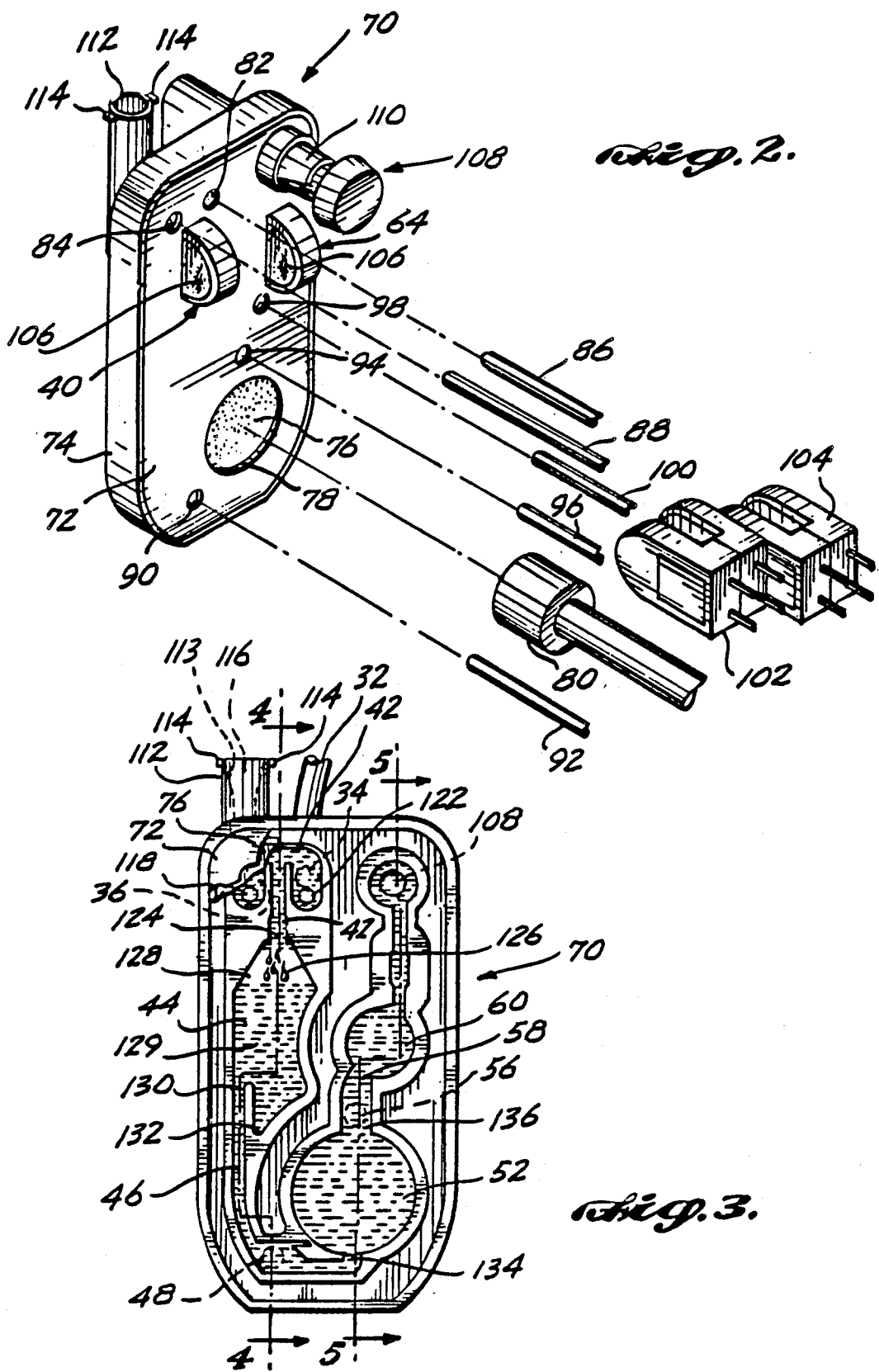

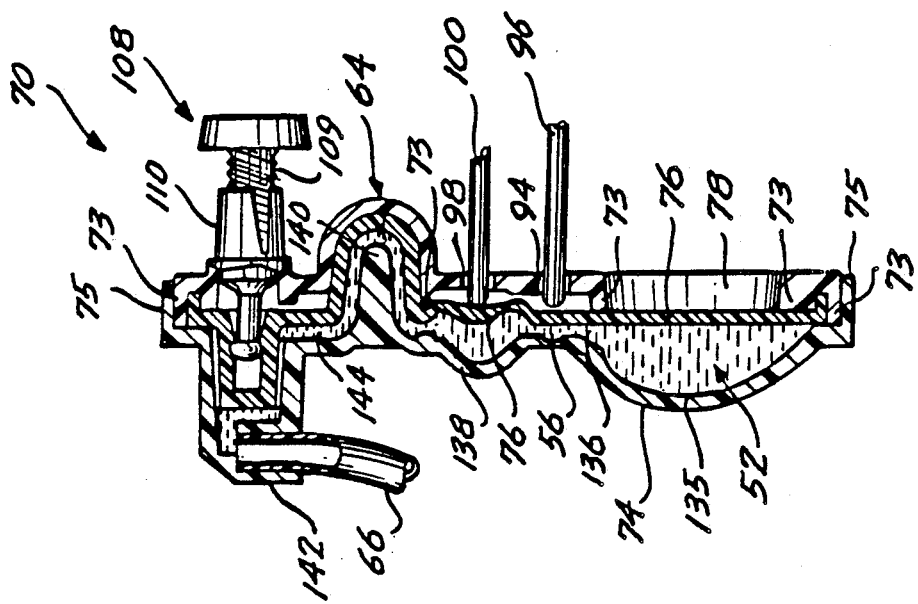
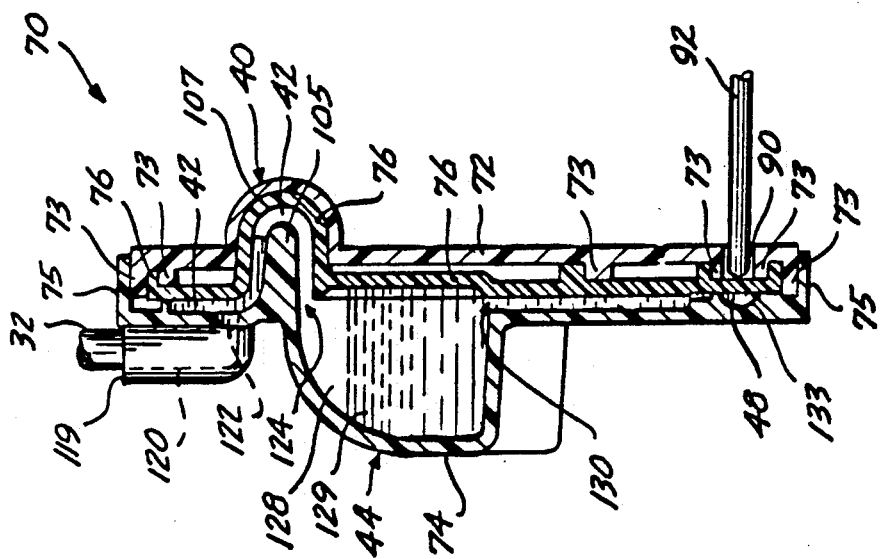

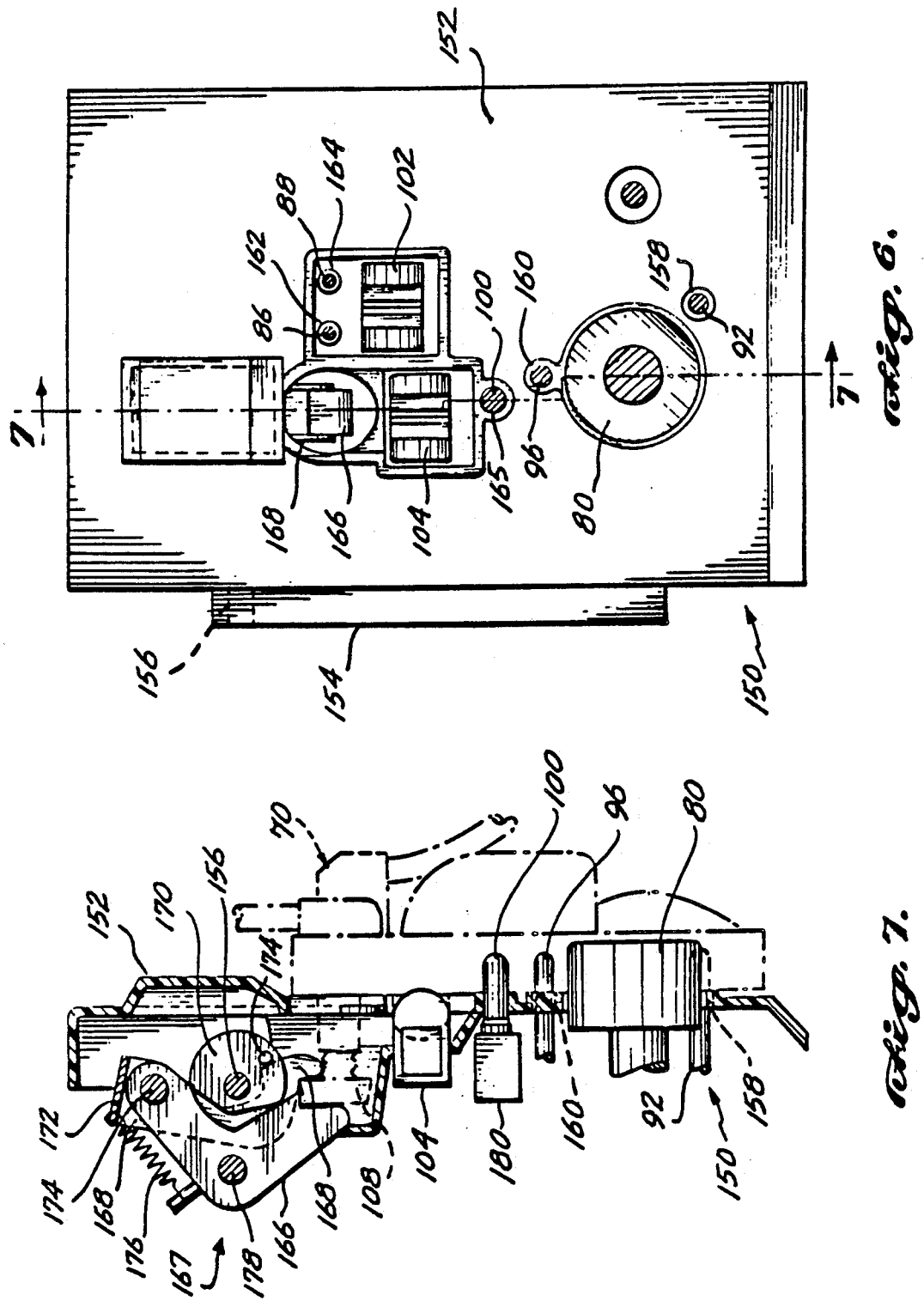

5,000,664

APPARATUS AND METHOD TO TEST FOR VALVE LEAKAGE IN A PUMP ASSEMBLY

TECHNICAL FIELD

This invention generally relates to a pump assembly including a plurality of valves and particularly, relates to apparatus and method for detecting leakage in any of the valves or the pump assembly.

BACKGROUND OF THE INVENTION

Disposable pump cassettes are frequently employed to infuse medicinal fluids into a patient. A pumping cassette may include a plastic housing having a front and a rear portion, between which an integral elastic membrane is encapsulated. One part of the housing has a number of ports through which actuators of a pump drive mechanism extend, interacting with the elastic membrane to control fluid flow through the cassette. A pump plunger on the drive unit presses against the membrane to reciprocatively pressurize liquid trapped in a pumping chamber formed between the membrane and the back of the housing. Similarly, actuator rods extend from the drive unit through ports in the housing, pressing against the membrane to interrupt fluid flow through valve passages formed in the back of the housing. A microprocessor in the pump drive controls the pump plunger and actuator rods to effect a desired rate of delivery of medicinal fluids to the patient, and in some units, is capable of selecting between a plurality of different sources by opening an appropriate selector valve in the cassette.

Selection of the source fluid and pumping rate or volume are normally determined by an operator programming the pump drive in response to a display prompt. Significant leakage through the valves in the pump cassette can create a potentially harmful variation from the programmed value in the quantity of medication actually delivered to a patient, or in the case of a leaking selector valve, may allow a medicinal fluid to enter the pump cassette when infusion of the fluid into the patient is not desired. Leakage of the valves or in other parts of the pump cassette, e.g., due to a poor seal between the elastic membrane and housing, is difficult or impossible to detect by visual inspection and may occur after the cassette was originally inspected for leaks during its manufacture. In view of the potential harm to the patient should significant leakage go undetected, there is clear justification for evaluating the leakage integrity of all valves and of the cassette assembly when it is first used to administer drugs, and perhaps at periodic intervals thereafter.

Apparatus and a method for detecting valve leakage in a pump cassette are disclosed in U.S. Pat. No. 4,657,490. A reciprocating plunger pressurizes and pumps fluid form a pumping chamber in the cassette described in this patent. To check for leakage, a stepping motor advances the plunger to elevate the pressure of liquid trapped in the pumping chamber between an inlet valve and an outlet valve. Attached to the plunger is a load cell that produces a signal indicative of the force required to pressurize the liquid trapped in the pumping chamber. If the signal produced by the load cell fails to indicate that an increase in force is required to elevate the pressure of the liquid, a system problem is indicated. Either the liquid supply is depleted, gravity feed of liquid is insufficient to fill the pumping chamber, or the inlet or outlet valve or both are leaking, allowing liquid to escape from the pumping chamber as the plunger is advanced.

Use of a load cell to detect multiple causes of system failure reduces the complexity of the device; however, this approach cannot determine which of the three possible problems has been detected. Moreover, in the disclosed method shown in the prior art, there is no provision for testing other valves in the cassette for leakage. The present invention provides a more effective apparatus to detect and identify valve leakage.

SUMMARY OF THE INVENTION

In accordance with the present invention, a pump assembly having the capacity to self test for leakage includes a pumping chamber in which liquid is pressurized during a pump cycle. An inlet valve is operative to periodically interrupt fluid flow into and out of the pumping chamber, with respect to a source of the fluid that is disposed upstream of the inlet valve. Fluid flow into and out from the pumping chamber through a delivery passage is controlled by an outlet valve, which periodically interrupts the fluid flow when the pump assembly is operating to pump fluid.

Downstream of the outlet valve is disposed a pressure sensor that senses the pressure of fluid in the delivery passage and produces a signal indicative of that pressure. Control means are included for controlling the pumping cycle and include self test means that are connected to receive the signal produced by the pressure sensor. The self test means are operative to fill the pumping chamber with the fluid, close the inlet and outlet valves, and to effect at least a partial pumping cycle to pressurize fluid in the pumping chamber. After a predetermined time interval, the self test means open the outlet valve to determine whether the pump assembly has leaked during the predetermined time interval, as a function of the signal produced by the pressure sensor after the outlet valve is opened.

When the outlet valve is open, a pressure pulse should propagate down the delivery passage from the pumping chamber. If the maximum amplitude of the pressure pulse is less than a predetermined value, the self test means are operative to detect that unacceptable leakage from a volume of fluid nominally trapped between the inlet and outlet valves has occurred during the predetermined time interval. Preferably, the self test means repetitively test for leakage and determine that the pump assembly is leaking only if a predetermined number of such tests indicate leakage.

The pump assembly may include selector valve means, disposed upstream of the inlet valve and connected n fluid communication therewith by an inlet passage. The selector valve means select at least one inlet port from among a plurality of inlet ports on the pump assembly for liquid communication with the inlet valve and pumping chamber.

Detection of leakage from a volume of fluid nominally trapped between selector valve means and the outlet valve is accomplished by the self test means, by filing the inlet passage and pumping chamber with fluid, closing the selector valve means and the outlet valve, and effecting at least a partial pumping cycle to pressure fluid in the inlet passage and in the pumping chamber. After a second predetermined time interval, the self test means close the inlet valve, then open the outlet valve, and determine if the pump assembly has leaked during the second predetermined time interval, as a function of the signal produced by the pressure sensor after the outlet valve is opened. If the maximum amplitude of the pressure pulse propagating down the delivery passage is less than a predetermined value, the self test means are operative to detect a leak in the pump assembly.

To effect an alternate preferred leakage test, the pump assembly includes an air trap reservoir disposed on the inlet passage, and an air-in-line sensor disposed in the inlet passage between the air trap reservoir and the selector valve means. The air-in-line sensor produces a signal indicative of the presence of air in the inlet passage where the air-in-line sensor is disposed and is connected to provide that signal to the self test means. If air is trapped in the air trap reservoir, the self test means are operative to determine whether the pump assembly is leaking by filling the inlet passage and pumping chamber with liquid, closing the selector valve means and the outlet valve, and effecting at least a partial pumping cycle to pressure liquid in the pumping chamber and in the inlet passage. The self test means then detect leakage form a volume of fluid nominally trapped between selector valve means and the inlet valve as a function of the signal produced by the air-in-line sensor. This signal indicates a leak upstream of the air-in-line sensor if, after the pumping cycle is initiated, the signal from the air-in-line sensor changes to indicate the presence of air rather than liquid, since the leakage causes air in the air trap reservoir to enter the air-in-line sensor.

A method including steps generally consistent with the functions implemented by the elements of the apparatus described above represents a further aspect of this invention.

BRIEF DESCRIPTION OF THE DRAWINGS

FIG. 2 is an isometric view of a disposable pumping cassette and a portion of a pump driver used to drive the pumping cassette and to actuate valves in the cassette;

FIG. 3 is a plan view of the cassette, with one side broken away to show its interior;

FIG. 4 is a cross-sectional view of the cassette, taken along a section line 4—4 of FIG. 3;

FIG. 5 is a cross-sectional view of the cassette, taken along a section line 5—5 of FIG. 3;

FIG. 6 is an elevational view of the pump drive, showing the front of the device, with its door removed to better disclose its layout;

FIG. 7 is a cross-sectional view of a portion of the pump drive front panel, taken along section line 7—7 of FIG. 6, and showing the cassette in phantom view, where it is attached to the pump drive during operation of the pump assembly;

DESCRIPTION OF THE PREFERRED EMBODIMENTS

Figure 1:
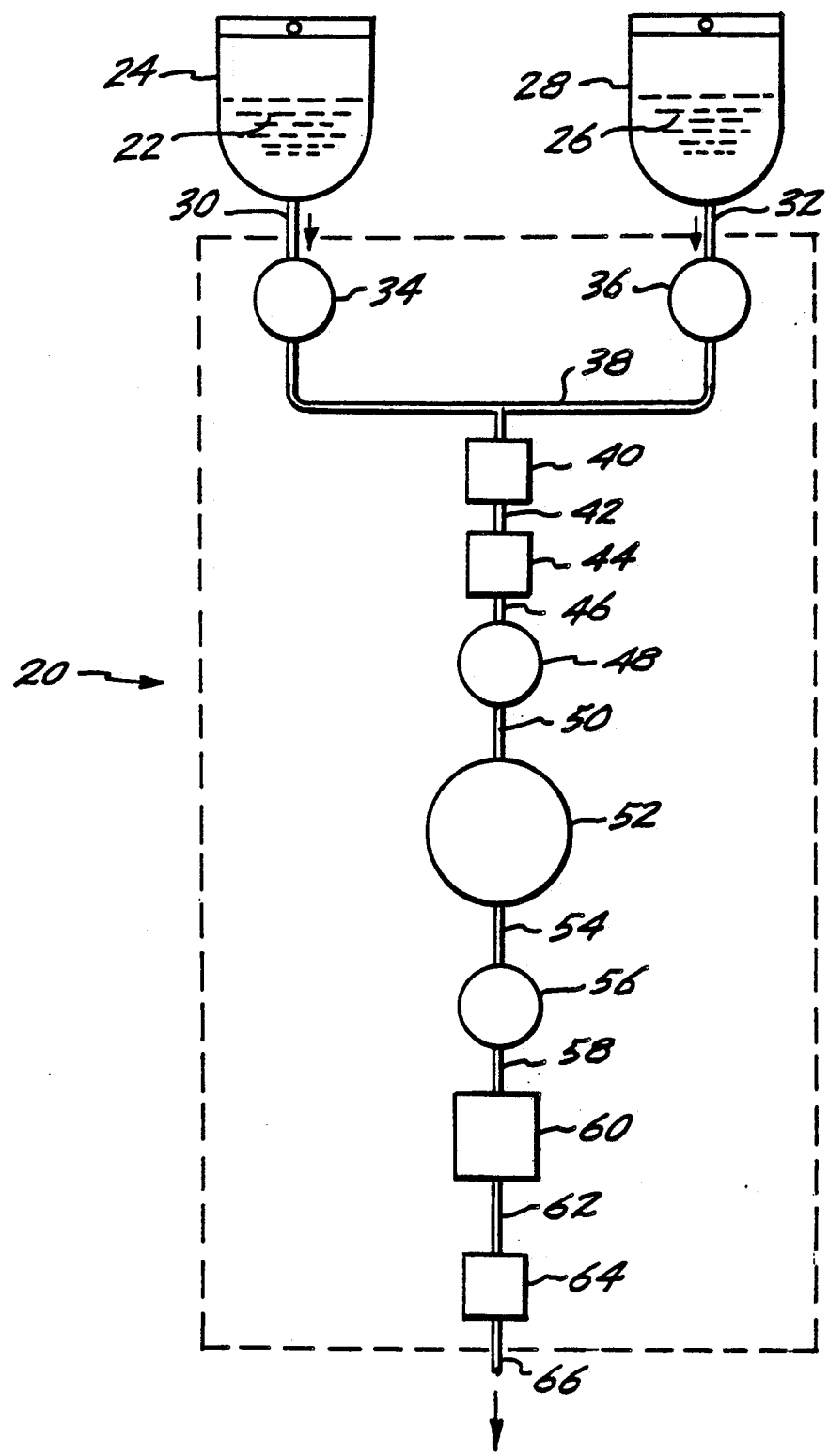
FIG. 1 schematically illustrates the flow path of a liquid through a pump assembly employing valve leak detection in accordance with the present invention.

A flow diagram for a pump apparatus used to administer liquids intravenously to a patient is shown schematically in FIG. 1, identified generally at reference numeral 20. Pump apparatus 20 is connected to selectively pump a first fluid 22, which is supplied from a reservoir bag 24, or a second fluid 26, supplied from a reservoir bag 28. Both reservoir bags 24 and 28 are typically elevated above pump apparatus 20, so that the first and second fluids freely flow downwardly toward the pump assembly; however, gravity flow is not required to prime the pump apparatus. Accordingly, a supply line 30 connects reservoir bag 24 to a primary valve 34, and similarly, a supply line 32 connects reservoir bag 28 to a secondary valve 36. Primary valve 34 and secondary valve 36 are both disposed within pump assembly 20 and are selectively controlled, as will be explained below, to permit either the first liquid or the second liquid to enter a manifold line 38, which connects both the primary and secondary valves to an air-in-line sensor 40.

A primary function of air-in-line sensor 40 is to detect the presence of air in either first fluid 22 or second fluid 26, to prevent air bubbles being delivered intravenously to a patient, since such bubbles, if sufficient in volume, could result in a fatal air embolism. With respect to the present invention, air-in-line sensor 40 has a secondary function, since it is also used to determine if the primary or secondary valve is leaking or to detect leakage from the volume of fluid disposed between the air-in-line sensor and the primary and secondary valves, as explained in detail below.

Downstream of air-in-line sensor 40 is disposed an air trap reservoir 44, which normally serves to capture any air bubbles. Air trap reservoir 44 is connected to air-in-line sensor 40 by an inlet passage 42. Similarly, an inlet passage 46 connects the outlet of the air trap reservoir to an inlet valve 48. Inlet valve 48 selectively enables fluid flow into a pumping chamber 52 through a passage 50.

A passage 54 connects the outlet of pumping chamber 52 to an outlet valve 56, which selectively controls fluid flow from pumping chamber 52, as described in greater detail below. Outlet valve 56 is connected through a delivery passage 58 to a pressure sensor 60. Pressure sensor 60 produces a signal indicative of the pressure of fluid within delivery passage 58, and is used in the present invention to detect leakage from the pump apparatus and to determine if inlet valve 48 or outlet valve is leaking. The pressure sensor can also be used to determine whether primary valve 34 or secondary valve 36 is leaking. Pressure sensor 60 is connected through a delivery passage 62 to an air-in-line sensor 64. Delivery passage 58 connects outlet valve 56 to air-in-line sensor 64, which performs only the function of detecting air bubbles in fluid delivered through a connected delivery tube 66, again to prevent air bubbles sufficient in volume to potentially cause an air embolism.

From FIG. 1, it will be apparent that a leak in either primary valve 34 or secondary valve 36 could permit either the first or second fluid, respectively, to flow into manifold line 38 when the presence of fluid from the nonselected source is not desired. Such leakage could potentially cause a dangerous amount of a medicinal fluid to be injected into a patient if leakage of the primary or secondary selector valve should be undetected, as explained above. In addition, any leakage through inlet valve 48 or outlet valve 56 or from pump apparatus 20 could either reduce the effective pumping rate of a medicinal fluid into a patient, or permit fluid flow through connected delivery tube 66 when pump apparatus 20 is supposed to be inoperative. Again, either condition could have potentially harmful effects if undetected.

FIGS. 2–5 illustrate a cassette 70, which comprises the pump apparatus described above. A housing face of cassette 70 includes a flange 73 that extends around its perimeter and around each of a plurality of cavities formed without a housing back 74 of the cassette. Housing back 74 also includes a flange around its perimeter, which sealingly connects to flange 73. Both a housing face 72 and housing back 74 are preferably molded from a rigid plastic such as polycarbonate or other suitable material. An elastomeric membrane 76 is positioned between housing face 72 and housing back 74 and is accessible through each of a plurality of ports formed in the housing face. For example, elastomeric membrane 76 is exposed at a plunger port 78 that is defined within the housing face. Behind the exposed portion elastomeric membrane 76 and formed in housing back 74 is pumping chamber 52. A plunger 80 is reciprocatively driven in and out of plunger port 78, actuating elastomeric membrane 76 so as to force fluid from pumping chamber 52 through open outlet valve 56, when inlet valve 48 is closed.

Housing face 72 also includes a primary valve port 82 and a secondary valve port 84 through which extend actuator rods 86 and 88, respectively. A rounded end on each of these actuator rods contacts elastomeric membrane 76, selectively controlling fluid flow through primary valve 34 and secondary valve 36. Similarly, an inlet valve port 90 provides an opening for an actuator rod 92 to depress elastomeric membrane 76 to control fluid through inlet valve 48, and an outlet valve port 94 servers a similar function with respect to an actuator rod 96, to control fluid flow through outlet valve 56. A somewhat different function is provided by a pressure sensor port 98, which allows a pressure sensor rod 100 to contact elastomeric membrane 76. Pressure sensor rod 100 transmits fluid pressure from a cavity defining pressure sensor 60, formed in housing back 74, to a strain gauge (not shown), which produces a signal indicative of fluid pressure.

Air-in-line sensors 40 and 64 extend outwardly from the outer surface of housing face 72. As shown in the cross section of FIG. 4, a finger 105 extends from housing back 74 into air-in-line sensor 40, and in conjunction with elastomeric membrane 76 defines inlet passage 42. On each side of air-in-line sensor 40, elastomeric membrane 75 bulges outwardly forming lobes 106. Similarly, as shown in FIG. 5, a finger 140 extends outwardly from housing back 74 into air-in-line sensor 64 to define delivery passage 62. Elastomeric membrane 76 also includes lobes 106 at each side of air-in-line sensor 64. A pair of ultrasonic transducers 102 and 104 (shown in FIG. 2) engage air-in-line sensors 40 and 64 so that a piezoelectric transmitter and piezoelectric receiver (neither shown) disposed at opposite sides of each transducer can come into contact with lobes 106. Elastomeric membrane 76 fits into a concave pocket 107 formed within housing face 72 as shown in FIG. 4, to provide an exposed passageway for engagement with ultrasonic transducer 102. An ultrasonic signal transmitted through the lobes determines the presence of an air bubble within the fluid passageway defined thereby.

Housing face 72 is also provided with a flow control 108 comprising a shaft 109 which is threaded into a projection 110. The end of shaft 109 engages elastomeric membrane 76, as shown in FIG. 5, to control fluid flow into delivery tube 66. Shaft 109 is threaded so that the flow control can be manually adjusted to set a desired flow rate for fluid into delivery tube 66 under gravity flow if a pump driver is not available. In addition, flow control 108 is normally set to block fluid flow through delivery tube 66 when cassette 70 is not locked in place within a drive mechanism, to prevent undesired delivery of medicinal fluids to a patient. A mechanism for opening flow control 108 is disclosed in further detail herein below.

Housing back 74 includes a secondary inlet 112, which either has an internal luer taper 113, provided with locking flanges 114 for connection with an appropriate luer fitting (not shown), or includes a resilient reseal plug (not shown) that is punctured with a needle. A secondary inlet passage 116 conveys fluid to an opening 118 formed within housing back 74. Elastomeric membrane 76 seals against housing back 74 immediately adjacent to opening 118 under the urging of actuator rod 88 to selectively stop fluid flow through opening 118.

Referring now to FIG. 4, a primary inlet 119 defines an inlet passage 120 through which fluid flows to an opening 122 formed within housing back 74. Immediately above opening 122 is disposed primary valve 34. The closure of primary valve 34 stops fluid flow through opening 122 from supply line 32. Fluid from secondary inlet 112 or primary inlet 119 flows through inlet passage 42 into air-in-line sensor 40, passes through the air-in-line sensor to a top reservoir inlet 124, and drips into air trap reservoir 44 as indicated by droplets 126. Air accumulates within a top section 128 of air trap reservoir 44 as shown at 129. Liquid accumulates in a bottom volume 132 of the reservoir, and flows through a bottom outlet 130 into inlet passage 46. If inlet valve 48 is open, fluid flows into the pumping chamber through a pumping chamber inlet 134. At the top of pumping chamber 52 is a pumping chamber outlet 136, disposed adjacent outlet valve 56. Outlet valve 56 is closed when elastomeric membrane 76 is sealed against housing back 74 under the urging of actuator rod 96. However, during a normal pumping cycle, valve 56 opens and fluid is displaced from pumping chamber 52 as elastomeric membrane 76 is forced toward housing back 74 by plunger 80. Displacement of the fluid from a recess 135 that forms the back of the pumping chamber, increases the pressure of the fluid in a pressure sensor recess 138, which comprises pressure sensor 60. The displaced fluid is forced around finger 140, through a delivery passage 144 and out an outlet 142, which is connected to delivery tube 66. (See FIG. 5.)

Turning now to FIGS. 6 and 7, parts of a pump driver as shown which relate to the present invention. A pump driver 150 includes a face plate 152. Cassette 70 is shown in phantom view in FIG. 7, illustrating how housing face 72 fits against face plate 152 of the pump driver, to enable engagement of flow control 108, to provide pumping action, and to effect actuation of the primary and secondary valves and inlet and outlet valves. Face plate 152 includes ultrasonic transducers 102 and 104, which are mounted at appropriate positions to fit over air-in-line sensors 40 and 64 of cassette 70 as previously disclosed with respect to FIG. 2. A driver door pivot arm 154 is mounted to a pivot shaft 156 on one side of face plate 152. Not shown in the drawing figures is a door to which driver door pivot arm 154 is attached, and which holds cassette 70 in place on face plate 152. The driver door connects to driver door pivot arm 154 causing the arm to rotate pivot shaft 156 as cassette 70 is locked in place by closure of the driver door.

Face plate 152 includes a plurality of openings, including an opening 158 through which actuator rod 92 extends, and an inverted key shape opening 160 through which plunger 80 and actuator rod 96 extend. Openings 162, 164, and 165 are provided for actuator rods 86, 88, and pressure sensor rod 100, respectively. Behind face plate 152, pressure sensor rod 100 is connected to a pressure transducer 180. Each of the actuator rods 86, 88, 92, and 96 are connected to levers actuated by motor driven cams (none of which are shown).

Also provided on face plate 152 is a flow control depressor 166, which comprises a portion of a flow shut-off assembly 167, shown in FIG. 7. Shut-off assembly 167 includes two arms 168 (only one shown) and a cam 170, which is connected at one end of pivot shaft 156. Flow control depressor 166 is mounted within a bracket 172, which connects arms 168 on each side of the flow control depressor. Pins 174 (only one shown) extend outwardly from both sides of cam 170, each contacting the edge of one of the arms 168, so that rotation of cam 170 transmits force through the pins to move the arms. A spring 176 is connected between bracket 172 and flow control depressor 166, urging arms 168 away form flow control 108 when pins 174 permit such movement as a result of rotation of cam 170 in the opposite direction. Each time that cassette 70 is engaged with face plate 152, driver door pivot arm 154 rotates pivot shaft 156, causing cam 170 to rotate so that arms 168 engage flow control 108, forcing the flow control to its full open position. Conversely, as the driver door pivot arm rotates to release cassette 70 from engagement with pump driver 150, cam 170 rotates pins 174 away from arms 168, and spring 176 causes arms 168 to pivot away from engagement with the flow control. As cam 170 continues to rotate, flow control depressor 166 is forced to pivot about a pivot shaft 178, engaging flow control 108 and forcing it to its fully closed position, just before cassette 70 is finally released from pump drier 10. As a consequence, fluid flow through cassette 70 under the force of gravity is blocked by flow control 108. After cassette 70 is removed from pump driver 150, flow control 108 can be manually adjusted to allow medicinal fluid to be administered to a patient at a controlled rate, if desired.

Since flow control 108 is forced to a full open position by shut-off assembly 167 when cassette 70 is mounted on pump driver 150, it is important that uncontrolled fluid flow through cassette 70 be prevented by some other mechanism. Accordingly, actuator rods 92 and 96 are mechanically interlocked to that at least one of the inlet and outlet valves is closed at all times that cassette 70 is mounted on pump driver 150. Since either inlet valve 48, or outlet valve 56, or both are closed at all times that cassette 70 is thus mounted, fluid cannot flow through the cassette, except as a result of controlled pumping action involving the selective opening and closing of the inlet and outlet valves.

Figure 10:
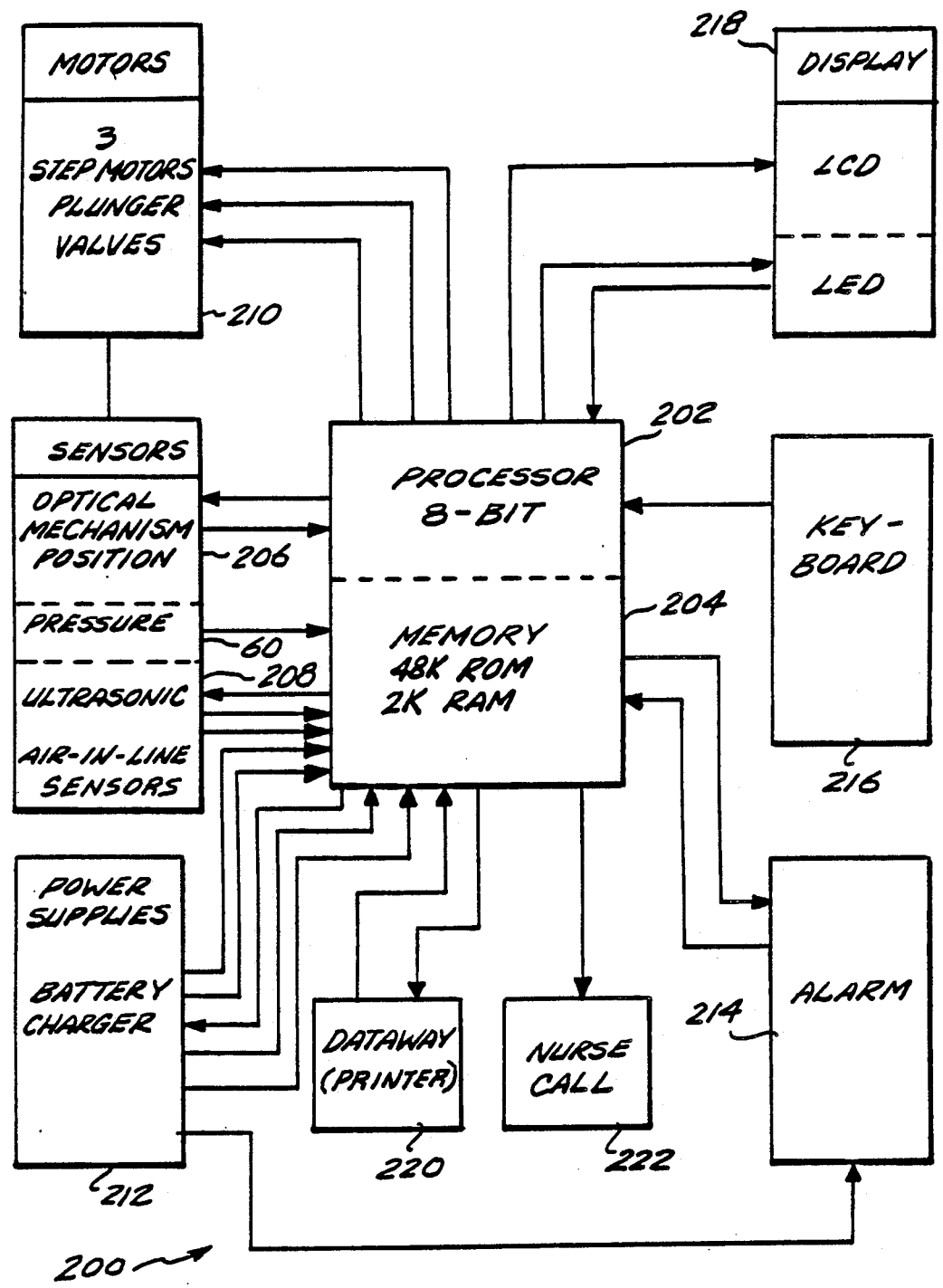
FIG. 10 is an electrical schematical block diagram of a pump drive and leak test control employed in the pump assembly.

Pump driver 150 is controlled to effect a desired pumping rate of selected medicinal fluids by a control 200, which is shown in a block diagram in FIG. 10. Control 200 is also programmed to conduct leakage tests of the inlet and outlet valves and the primary and secondary valves in accordance with the present invention. An 8-bit microprocessor 202 in the control responds to programmed instructions stored in a read-only memory (ROM) and maintains values temporarily in a random access memory (RAM) as indicated by a memory block 240, associated with microprocessor 202. A plurality of signal lines interconnect each of the other blocks shown in FIG. 10 to microprocessor block 202 and memory block 204, in a manner well known by those or ordinary skill in the art. A key aspect of the present invention comprises output signals from pressure sensor 60, and from the ultrasonic air-in-line sensor, collectively identified as a sensor block at reference numeral 208. In addition, a plurality of optical mechanism position sensors 206, are connected to microprocessor 202 for monitoring the operation of pump driver 150. Since the optical mechanism position sensors are not particularly relevant to the subject mater of the present invention, details concerning their function and structure are omitted herein. Also connected to microprocessor 202 are three stepping motors 210, which effect operation of plunger 80 and actuator rods 86, 88, 92 and 96 for the primary and secondary valves and the inlet and outlet valves, respectively.

Microprocessor 202 thus controls the plunger and each of the valves in cassette 70 according to preprogrammed instructions, and consistent with input data provided the microprocessor from a keyboard 216. The operator enters data such as the pumping rate desired in response to prompts created on a display 218, which includes both a liquid crystal display (LCD) and light emitting diodes (LEDs). Power supplies 212 provide appropriate voltages at necessary current levels to each of the active components in control 200 and include a battery charger to maintain a backup battery (not separately shown) in the event that power is interrupted from an AC line source. A data way 220 is provided on control 200 to enable bi-directional data exchange with an external device, for example, a printer. Where appropriate, microprocessor 202 can initiate a nurse call as shown by a block 222, to summon help in the event that action by medical personnel is required. In addition, control 200 includes an alarm 214, which may comprise both visual and audible signals, energized when emergency conditions are detected, such as a leak in one of the primary, secondary, inlet, or outlet valves.

Figure 8A:
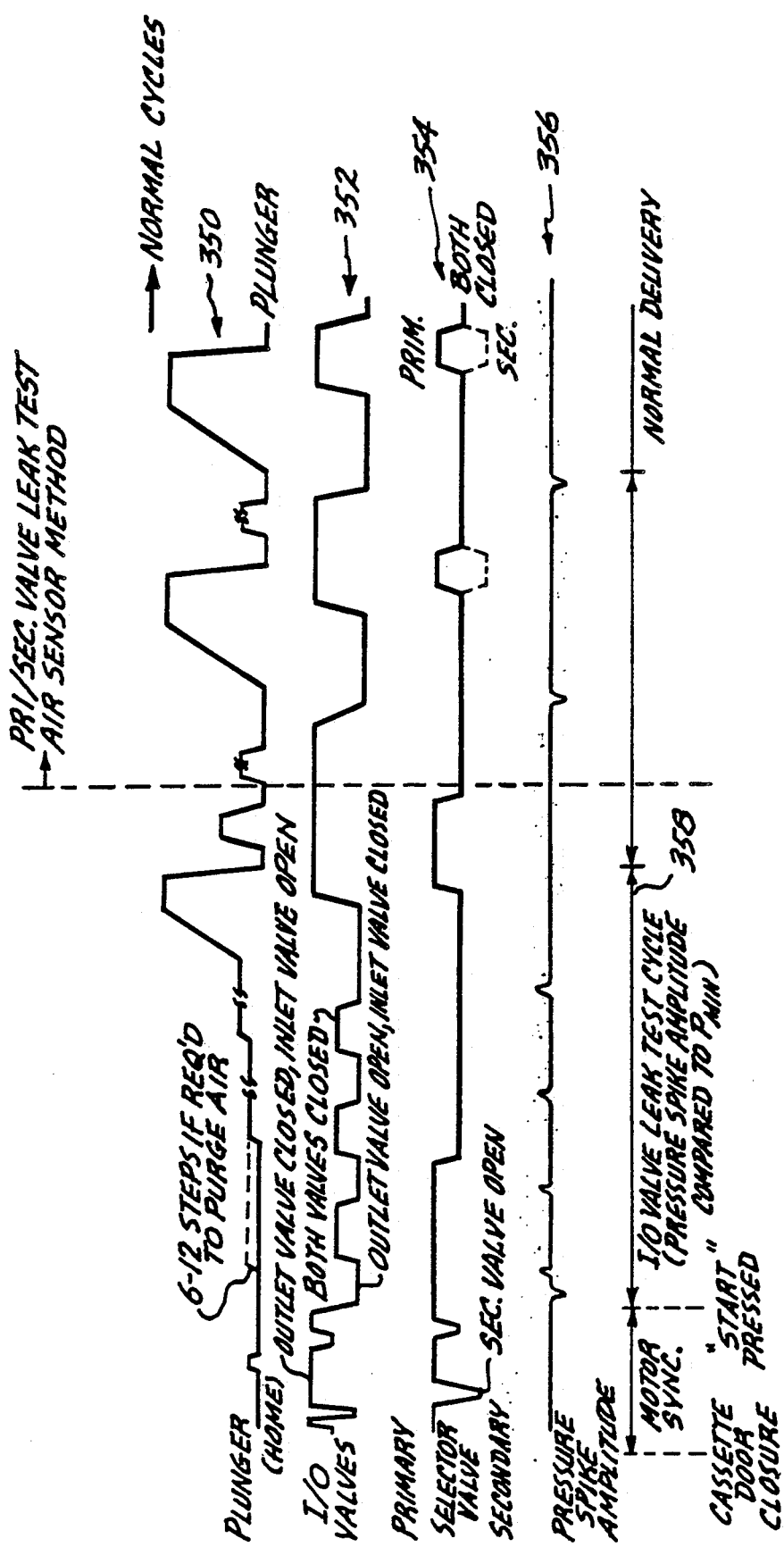
FIGS. 8A and 8B graphically represent the time sequence of operation of the pump assembly during tests for leaks in the valves of the cassette.
Figure 8B:
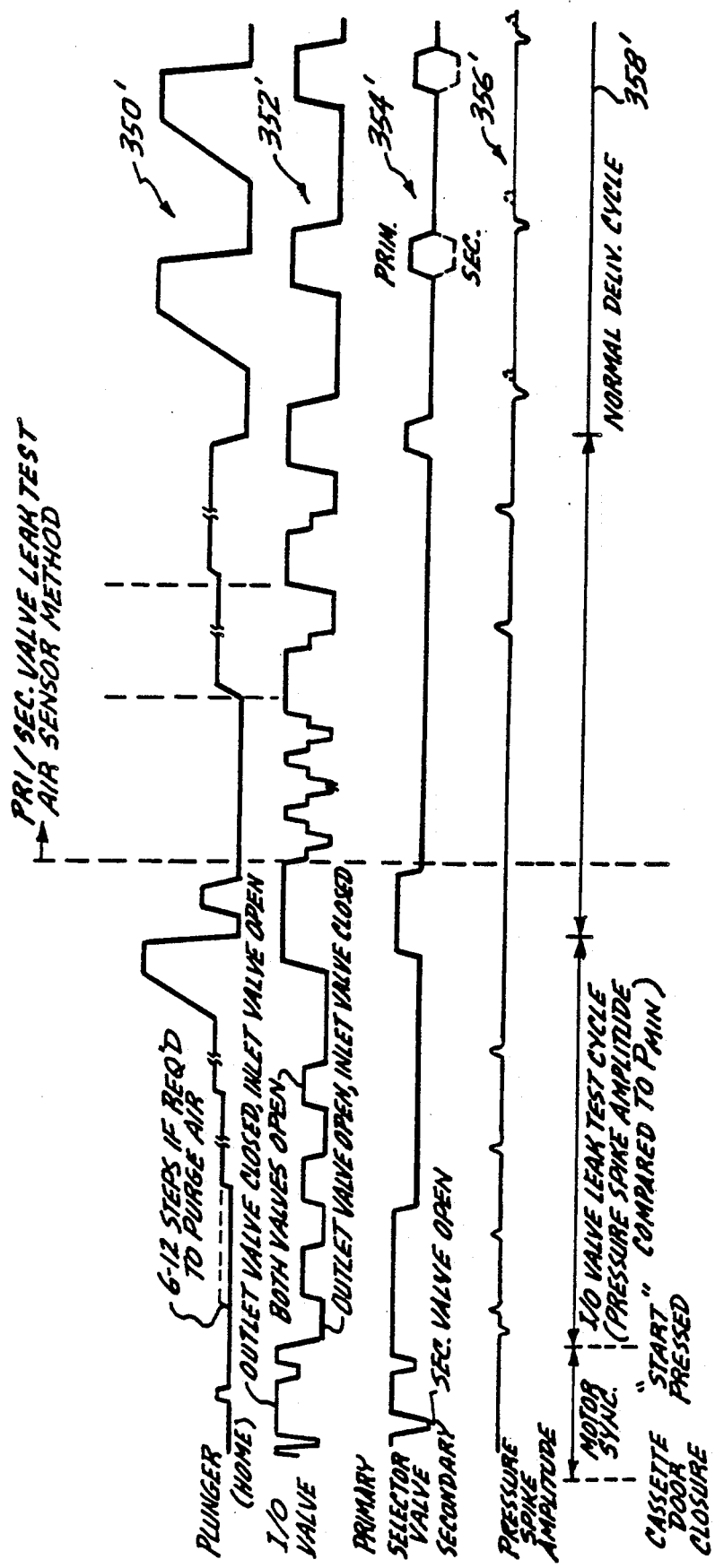

Stored in ROM within memory block 204 are the leak detection algorithms implemented by microprocessor 202. The logic implemented in these algorithms is shown in a flow chart in FIGS: 9A-9C. Timing for the valve leakage test (and other operations of pump apparatus 20), are shown in FIGS. 8A and 8B. Reference to the timing charts assists in understanding the valve integrity test logic shown in the flowcharts. The first leakage test performed in cassette 70 after start-up uses the logic illustrated in FIG. 9A to determine whether inlet valve 48 or outlet valve 56 (or the portion of cassette 70 defining the fluid volume between these two valves) is leaking. The left sides of both FIG. 8A or 8B corresponds to the timing for determining leakage of fluid nominally trapped between the inlet and outlet valves, while the right sides of the figures show two different methods for determining leakage of fluid nominally trapped between the primary and secondary valves and the outlet valve. In the timing chart, FIG.

8A, a line 350 (top line in the timing chart) illustrates the relative position of plunger 80, the lowest vertical points along line 350 indicating the position of the plunger when it is fully withdrawn, and the highest vertical points along the line representing the fully extended stroke position of plunger 80, which displaces fluid from pumping chamber 52.

A line 352 indicates the condition of inlet valve 48 and outlet valve 56, the center vertical position along line 352 indicating that both valves are closed, the highest vertical position indicating that outlet valve 56 is closed and inlet valve 48 is open, and the lowest vertical position indicating that the outlet valve is open while the inlet valve is closed. The condition of primary and secondary valves are similarly shown by a line 354, wherein the center vertical elevation of the line indicates that both valves are closed, the highest vertical pints on the line indicate the primary valve is open, and the lowest indicating that the secondary valve is open.

The signal produced by pressure sensor 60 is shown on a line 356, wherein a positive spike indicates a pressure pulse detected at the point where pressure sensor 60 is disposed, downstream of pumping chamber 52 and outlet valve 56, due to a pressurized fluid wave propagating downstream of the outlet valve. A line 358 generally indicates the cycle that is being Implemented. For example, on the left side of line 358, a motor synchronization cycle is implemented to ensure that the valves and plunger motor are properly synchronized. A check of the inlet and outlet valve leak integrity follows the motor synchronization cycle, beginning with an operator depressing a start button (not shown) on keyboard 216. This check also detects leakage of cassette 70 due to failure of the seal between elastomeric membrane 76 and housing back 74, e.g., around pumping chamber 52.

Figure 9A:
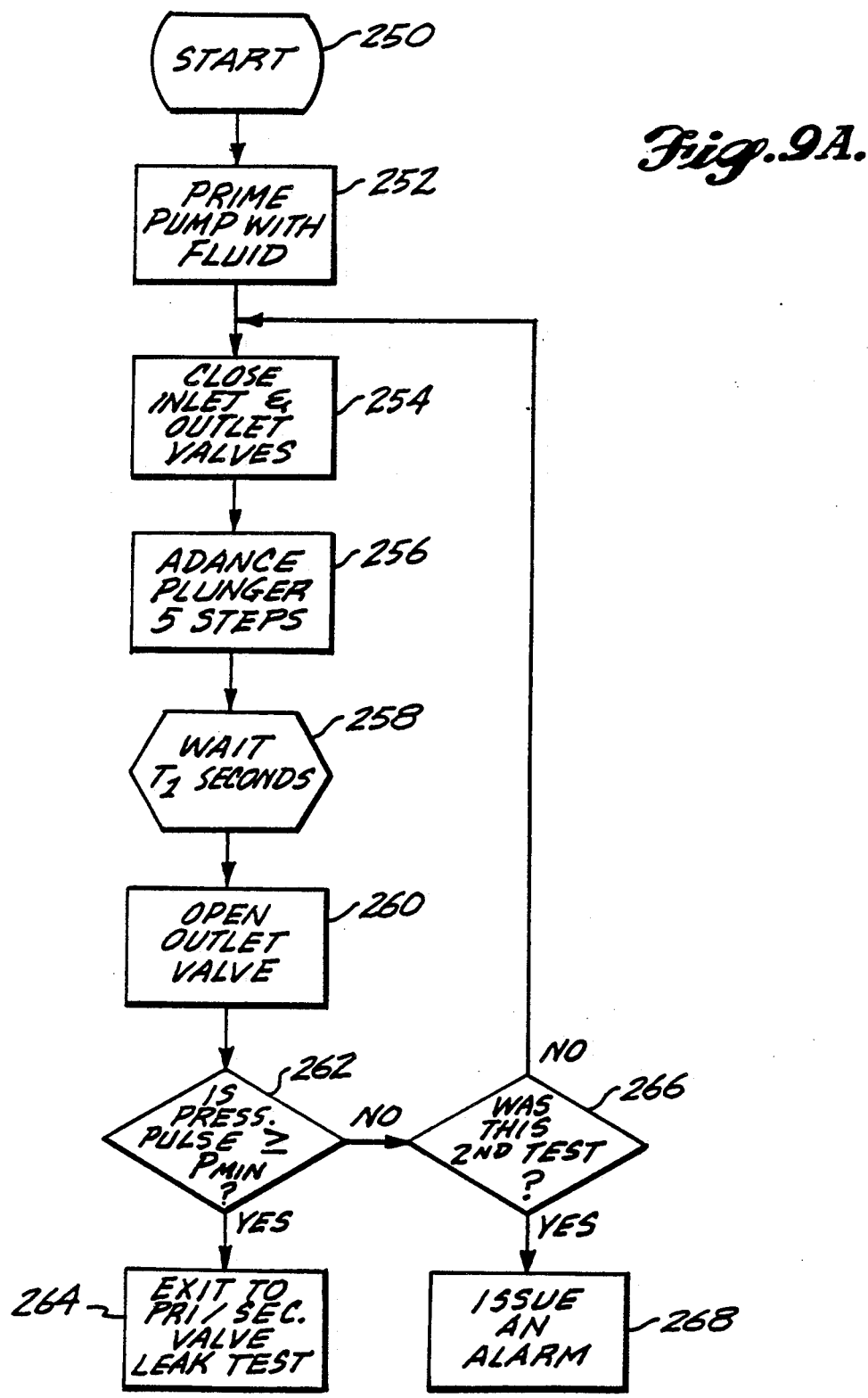
FIGS. 9A, 9B, and 9C respectively illustrate the logic used for testing the input-output valves for leaks, primary and secondary valves for leaks using an air-in-line sensor, and tests of the primary and secondary valves for leakage using the pressure sensor.

As shown in FIG. 9A, the algorithm begins with the start initiated in a block 250 and proceeds to a block 252 wherein cassette 70 is primed with fluid (either the primary or secondary) that is to be delivered to the patient. To prime cassette 70 with primary fluid, pumping chamber 52 may be filled by gravity feed prior to installation in the drive unit, or by pumping air from the cassette before the IV line is connected to the patient. As shown by line 350 (FIG. 8A) after the priming operation, plunger 80 is initially fully withdrawn from pumping chamber 52. IN a block 254, both the inlet and outlet valves are closed so that fluid is trapped within pumping chamber 52 between the two valves. In a block 256, plunger 80 is advanced by five steps of the stepping motor that drives it, which corresponds to a holding pressure in pumping chamber 52 of approximately 10 psi. This pressure is held for a period of time ragging between two and ten seconds, as a function of the programmed delivery rate for the fluid, as shown in Table 1 below. For a pumping rate less than 130 ml per hour, a maximum of ten seconds holding time is provided; however, for rates between 130 and 1,000 mls per hour, the holding time corresponds to a leakage equal to approximately 5% of the pumping rate.

TABLE 1

| RATE ml/hr | I/O VALVE HOLD TIME $T_1$ (SECONDS) |
| --- | --- |
| Up to 120.0 | 10.0 |
| Up to 130.0 | 9.0 |
| Up to 150.0 | 8.0 |
| Up to 100.0 | 7.0 |

TABLE 1-continued

| RATE ml/hr | I/O VALVE HOLD TIME $T_1$ (SECONDS) |
| --- | --- |
| Up to 210.0 | 6.0 |
| Up to 270.0 | 5.0 |
| Up to 360.0 | 4.0 |
| Up to 540.0 | 3.0 |
| Up to 999.0 | 2.0 |

At the end of the time interval indicated as $T_1$, in blocks 258 and 260, outlet valve 56 is opened, while inlet valve 48 remains closed. When outlet valve 56 is opened, a dynamic pressure pulse propagates through delivery passage 58, downstream of outlet valve 56, and is sensed by pressure sensors 60. The amplitude of the pressure pulse should exceed a predetermined minimum, unless either (or both) the inlet or outlet valve or the cassette has leaked during the holding period, $T_1$. In a block 262, microprocessor 262 determines if the pressure pulse is equal or greater than a predetermined value, $P_{min}$, and if so, the software logic proceeds to a block 264, to continue at the top of FIG. 9B, wherein the primary and secondary valve are checked for leakage.

Assuming that the pressure pulse is less than $P_{min}$ in block 262, a block 266 determines if there has been a previous test of the inlet and outlet valve leak integrity, and if not, the logic proceeds back to repeat the inlet/outlet (I/O) valve leak test, starting with block 254. Alternatively, fi the pressure pulse is less than or equal to $P_{min}$ in a second test, the logic proceeds to a block 268, wherein an alarm is effected, comprising either an audible or visual signal to alert the operator that excessive leakage has been detected. While determination of I/O valve or cassette 70 leakage only depends on the results of two such tests in the preferred embodiment, it may be made to depend on the results of more than two consecutive tests. Line 350 shows that at the conclusion of the I/O valve leak test, assuming that the valves and cassette are not leaking, fluid is delivered through the open outlet valve by completion of the plunger stroke.

Figure 9B:
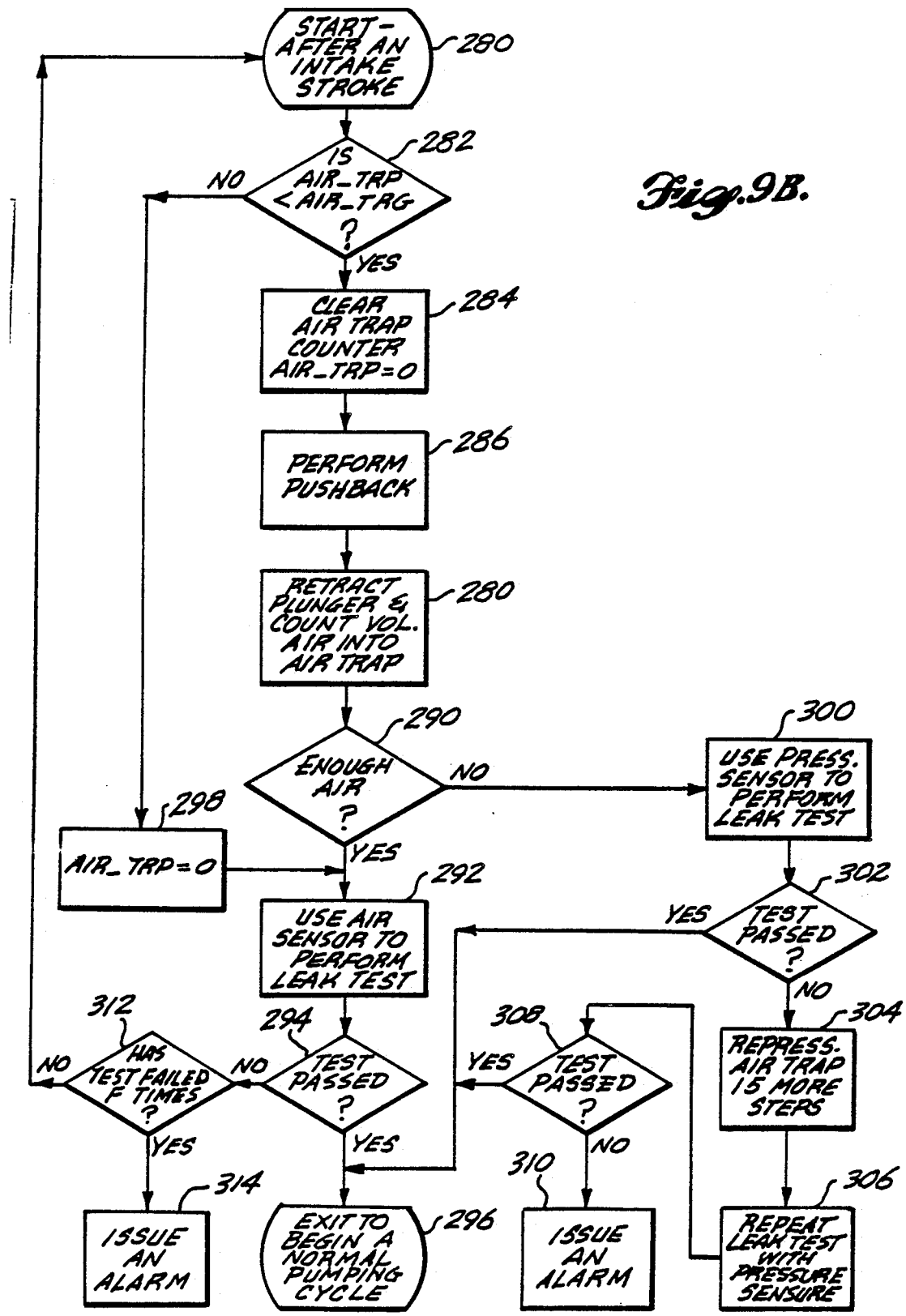

In the portion of the flow chart shown in FIG. 9B, a first preferred method for testing the primary and secondary valves for leakage uses the signal output from air-in-line sensor 40. This test also detects leakage from the fluid passages of cassette 70 that are between air-in-line sensor 40 and the primary and secondary valves. Following the completion of the delivery stroke at the end of the inlet/outlet valve leak test cycle, the outlet valve closes and the inlet valve opens so that as plunger 80 pulls back to its fully retracted position, fluid again fills pumping chamber 52, as indicated in a block 280 in the flow chart. In a block 282, the logic determine if a value designated "Air Trp" is less than a value "Air Trg". These values are determined from a previous test of the primary and secondary valves, if one was made. If such a test had not previously been made, or if the results were positive, the logic proceeds to a block 284, wherein a counter having the count $Air_{13}Trp$, indicative of the amount of air trapped in the air trap reservoir is cleared, i.e., set equal to zero. Then, in a block 286, plunger 80 performs a push back as the stepping motor that drives it advances through twenty steps. Fluid is forced from pumping chamber 52 in retrograde direction, through the open inlet valve, displacing fluid within the air trap reservoir 44. Any air within air trap reservoir 44 is thus forced back through air-in-line sensor 40 during the push back operation. Thereafter, microprocessor 202 waits for approximately 100 milliseconds for settling to occur and retracts plunger 80 by twenty steps of its stepping motor, placing it back to its fully retracted position. With each step that plunger 80 is retracted, microprocessor 202 checks to see if the signal output from air-in-line sensor 40 corresponds to the presence of air or liquid, and accumulates the number of such steps during which the air-in-line sensor detects air. The total step count for air within air trap reservoir 44 can range between zero and twenty, depending upon the number of steps of the stepping motor during which air was detected within air-in-line sensor 40. This operation of the algorithm is referenced in a block 288. (If no liquid in the air trap reservoir, a plurality of pumping cycles are initiated to draw liquid into cassette 70 and the push back operation is repeated.)

Subsequently, in a block 290, if the air count is greater than or equal to a predetermined value, preferably four in the preferred embodiment, sufficient air is detected to perform a primary/secondary valve leak test using the air-in-line sensor. This affirmative response to the question posed in block 290 causes the logic to proceed to a block 292 to perform the leak test using the air-in-line sensor. An air count equal to four corresponds to approximately 16 microliters of air within the air trap reservoir in the preferred embodiment. However, before initiating the leak test using air-in-line sensor 40, liquid must be detected within the air-in-line sensor. To perform the leak test using the air-in-line sensor, both primary and secondary valves are closed; inlet valve 48 remains open and outlet valve 56 closed. Microprocessor 202 causes plunger 80 to advance, pressurizing fluid within pumping chamber 52 and other internal passages of cassette 70, back through air-in-line sensor 40. If during a period of time, $T_2$, which is determined in accord with the programmed pumping rate as shown in Table 2 below, the signal output from air-in-line sensor has not changed from indicating that liquid is present to indicating that air has entered inlet passage 42, then neither the primary nor secondary valve has leaked and fluid has not leaked from cassette 70 upstream of air-in-line sensor 40. An inquiry in a block 294 to determine whether the primary and secondary valves (and cassette 70) have passed the test may be answered in the affirmative. With an affirmative answer, the logic proceeds to a block 296 to begin the normal pumping cycle. Alternatively, if air is detected within air-in-line sensor 40 during the $T_2$ holding period, the logic returns to block 280, following a full stroke by plunger 80, to provide for another intake stroke.

TABLE 2

| RATE ml/hr | PRIMARY/SEC. VALVE HOLD TIME $T_1$ (SECONDS) |
|---|---|
| Up to 100.0 | 15.0 |
| Up to 110.0 | 13.0 |
| Up to 120.0 | 12.0 |
| Up to 140.0 | 11.0 |
| Up to 150.0 | 10.0 |
| Up to 170.0 | 9.0 |
| Up to 200.0 | 8.0 |
| Up to 230.0 | 7.0 |
| Up to 280.0 | 6.0 |
| Up to 350.0 | 5.0 |
| Up to 460.0 | 4.0 |
| Up to 700.0 | 3.0 |
| Up to 999.0 | 2.0 |

As shown in Table 2, the hold time ranges from a maximum fifteen seconds for a pumping rate up to 100 milliliters per hour to two seconds for a pumping rate of about 1000 milliliters per hour. For all pumping rates in excess of 100 milliliters per hour, the hold time corresponds to a maximum allowed leakage equivalent to approximately 10% of the pumping rate (for the preferred embodiment of cassette 70). With respect both to Table 1 and Table 2 different holding times may be provided within the algorithm, to accommodate maximum allowed leakages equal to a different percentage of the pumping rate.

Figure 9C:
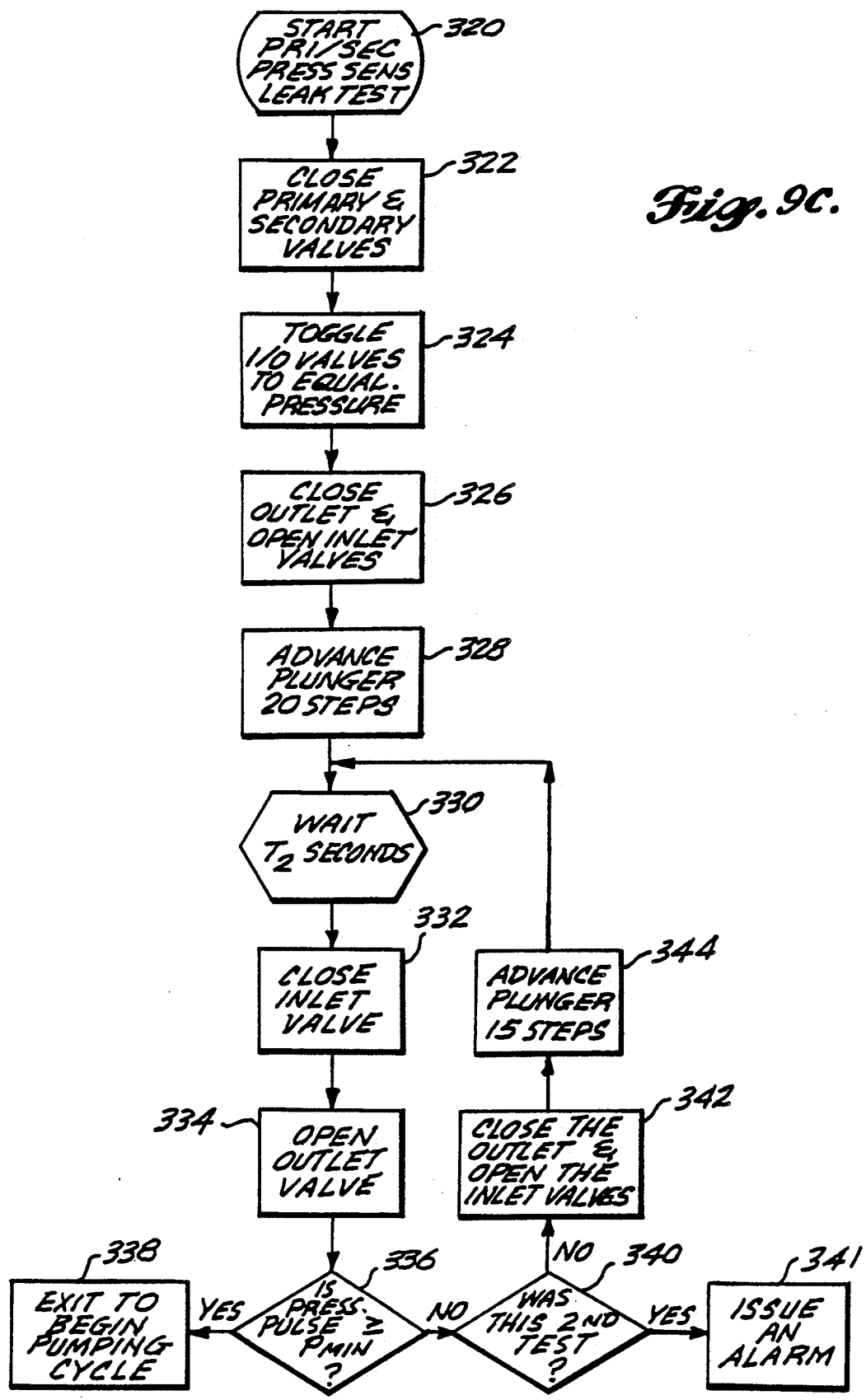

Referring back to the flow chart in FIG. 9B, if the answer to the inquiry in block 294 is negative, a block 312 determines whether the test has failed a predetermined number, F, times and if so issues an alarm in a block 314. If not, the test is repeated, starting with block 280. In block 290, if insufficient air is present to perform the test for leakage in primary and secondary valves 34 and 36, respectively, the logic reverts to a block 300, to initiate the test using pressure sensor 60. Tests of the primary and secondary valves using pressure sensor are shown in FIG. 9C, described below. Following the test of the primary and secondary valves using the pressure sensor, a block 302 determines if the test was passed, and, if so, the logic continues to block 296, where it exits to begin a normal pumping cycle. Alternatively, in a block 304, the test of the primary and secondary valves using the pressure sensor is repeated, by advancing plunger 80 through fifteen more steps of its stepping motor. In a block 306 the leak test is repeated as shown in FIG. 9C, using pressure sensor 60. In a block 308, if the test was passed, the logic proceeds again to block 296; otherwise, the logic proceeds to a block 310 to issue an alarm.

FIG. 9C and the timing diagrams in FIG. 8B illustrate the logic used to test primary valve 34 and secondary valve 36 and the portion of cassette 70 between these two valves and outlet valve 56 for leakage integrity as a function of the signal output from the pressure sensor 60. This test is similar to that used to test the leakage integrity of inlet valve 48 and outlet valve 55. Logic in FIG. 9C starts with a block 320, entered as provided in blocks 300 and 306 of FIG. 9B. From block 320, the logic proceeds to a block 322 in which the primary and secondary valves are closed. Next, inlet valve 48 and outlet valve 56 are toggled between their opened and closed conditions through an intermediate position in which they are both closed (preferably at least six times) to equalize internal pressure within cassette 70. At the conclusion of the toggling operation in a block 324, the inlet and outlet valves satisfy the condition in a block 326, i.e., outlet valve 56 is closed and inlet valve 48 is open. Plunger 80 is then advanced twenty steps of its stepper motor in a block 328, pressurizing fluid within pumping chamber 52 and in the internal passages of cassette 70, all the way back to both primary valve 34 and secondary valve 36. In a block 330, microprocessor 202 waits for a period of time equal to two to fifteen seconds, again depending upon the delivery rate programmed by the user (see Table 2). Finally, in blocks 332 and 334, inlet valve 48 is closed and outlet valve 56 is opened. If a pressure pulse with an amplitude greater than or equal to a predetermined value, $P_{min}$ is detected propagating through the fluid downstream of outlet valve 56 by pressure sensor 60, a block 336 determines that neither the primary nor secondary valves nor cassette 70 are leaking. Clearly, if fluid is leaking through either of these valves, or from the volume of fluid nominally trapped between the primary and secondary valves and the outlet valve, the pressure of fluid trapped in pumping chamber 52 is reduced, so that when the outlet valve is open, the amplitude of the pressure pulse that propagates to pressure sensor 60 is significantly reduced.

Assuming that neither the primary and secondary valves nor cassette 70 have leaked during the preceding test, in block 338, the logic initiates the normal pumping cycle. Upon failure to pass the leak test in block 336, the logic proceeds to a block 340, which determines if this is the second time the test has failed, and, if so, issues an alarm in a block 341. Otherwise, logic proceeds to a block 342 in which the outlet valve is closed and the inlet valve opened. In a block 344, the plunger advances fifteen more steps before proceeding to block 330, where the pressure is again held for the predetermined time period, $T_2$. Blocks 340, 342, and 344 in FIG. 9C thus correspond to blocks 308, 310, an 304 in FIG. 9B.

It will be apparent that the primary and secondary valves and cassette 70 could be tested for leakage using only pressure sensor 60, without using the air-in-line sensor method. However, the air-in-line sensor method is more sensitive in determining leakage through the primary and secondary valves than is the method using pressure sensor 60 if air is present in the cassette. However, if little or no air is present in the cassette, the test using the pressure sensor is preferred. Furthermore, leakage tests of the primary and secondary valves using the air-in-line sensor are independent of tests for leakage integrity of the inlet and outlet valves. However, leakage of the inlet or outlet valves or of cassette 70 will affect the results of leakage tests on the primary secondary valves using pressure sensor 60. For this reason, it is best to determine that the volume of fluid trapped between the inlet and outlet valves is not leaking before testing the leakage integrity of the primary and secondary valves and the remainder of cassette 70, particularly if the pressure sensor method is used.

While the present invention has been disclosed with respect to preferred embodiments, those of ordinary skill in the art will understand that further modifications thereto may be made within the scope of the claims that follow below. Accordingly, it is not intended that the invention in any way be limited by the disclosure, but instead that it be determined entirely by reference to the claims.

The embodiments of the invention in which an exclusive property or privilege is claimed are defined as follows:

1. A pump assembly having the capacity to self test for leakage, comprising:
   (a) a pumping chamber in which a fluid is pressurized during a pumping cycle;
   (b) an inlet valve that periodically interrupts fluid flow into and out of the pumping chamber, with respect to a source of the fluid disposed upstream of the inlet valve;
   (c) an outlet valve that periodically interrupts fluid flow into and out of the pumping chamber, with respect to a delivery passage through which pressurized fluid flows when the pump assembly is operating to pump the fluid;
   (d) a pressure sensor, disposed downstream of the outlet valve and operative to sense the pressure of the fluid and to produce a signal indicative of that pressure; and
   (e) control means for controlling the pumping cycle, including self test means connected to receive the signal produced by the pressure sensor for:
      (i) filling the pumping chamber with the fluid;
      (ii) closing the inlet and the outlet valves;
      (iii) effecting at least a partial pumping cycle to pressurize fluid in the pumping chamber and thereafter terminating the pumping cycle;
      (iv) after a predetermined time interval during which the pump assembly is inactive to further pressurize fluid in the pumping chamber, opening the outlet valve; and
      (v) determining whether the pump assembly has leaked during the predetermined time interval, as a function of the signal produced by the pressure sensor after the outlet valve is opened.

2. The pump assembly of claim 1, wherein said signal produced by the pressure sensor is indicative of a pressure pulse caused by propagation of a pressurized fluid wave down the delivery passage from the pressure chamber when the outlet valve is opened.

3. The pump assembly of claim 2, wherein unacceptable leakage from a volume of fluid nominally trapped between the inlet and outlet valves during the predetermined time interval is detected by the self test means if the maximum magnitude of the pressure pulse is less than a predetermined value.

4. The pump assembly of claim 1, wherein the control means are further operative to effect an alarm if the self test means determine that the pump assembly has leaked during the predetermined time interval.

5. The pump assembly of claim 4, wherein the self test means are operative to repetitively test for fluid leakage, and to determine that the pump assembly is leaking only if a predetermined number of such tests indicate leakage.

6. The pump assembly of claim 1, further comprising selector valve means, disposed upstream of the inlet valve and connected in fluid communication therewith by an inlet passage, for selecting at least one inlet port from among a plurality of inlet ports on the pump assembly for connection to the source supplying the fluid to the inlet valve and pumping chamber.

7. The pump assembly of claim 6, wherein the self test means are further operative to detect leakage by:
   (a) filling the inlet passage and pumping chamber with fluid;
   (b) closing the selector valve means and the outlet valve;
   (c) effecting at least a partial pumping cycle to pressurize fluid in the inlet passage and in the pumping chamber;
   (d) after a second predetermined time interval, closing the inlet valve and then opening the outlet valve; and
   (e) determining whether the pump assembly has leaked during the second predetermined time interval, as a function of the signal produced by the pressure sensor after the outlet valve is opened.

8. The pump assembly of claim 7, wherein said signal produced by the pressure sensor is indicative of a pressure pulse caused by propagation of a pressurized fluid wave down the delivery passage chamber when the outlet valve is opened.

9. The pump assembly of claim 8, wherein unacceptable leakage from a volume of fluid nominally trapped between the selector valve means and the inlet valve during the second predetermined time interval is detected by the self test means if the maximum magnitude of the pressure pulse is less than a predetermined value.

10. The pump assembly of claim 6, further comprising an air trap reservoir disposed on the inlet passage, and an air-in-line sensor disposed in the inlet passage between the air trap reservoir and the selector valve means, said air-in-line sensor being operative to produce a signal indicative of the presence of air in the inlet passage where said air-in-line sensor is disposed and being connected to provide that signal to the self-test means.

11. The pump assembly of claim 10, wherein the self test means are further operative to alternatively determine whether unacceptable leakage form a volume of fluid nominally trapped between the selector valve means and the outlet valve has occurred, if air is trapped in the air reservoir, by:
(a) filling the inlet passage and pumping chamber with a liquid;
(b) closing the selector valve means and the outlet valve;
(c) effecting at least a partial pumping cycle to pressurize the liquid in the pumping chamber and in the inlet passage; and
(d) determining whether the selector valve means are leaking as a function of the signal produced by the air-in-line sensor.

12. The pump assembly of claim 11, wherein a change in the signal produced by the air-in-line sensor indicating the presence of air flowing from the air trap reservoir into the inlet passage where the air-in-line sensor is located, after said at least partial pumping cycle is initiated is determinative of a leak in the pump assembly.

13. The pump assembly of claim 11, wherein the self test means are further operative to effect a plurality of pumping cycles before closing the selector valve means and the outlet valve, in order to clear any air initially present in the inlet passage where the air-in-line sensor is disposed.

14. The pump assembly of claim 11, wherein the self test means are operative to determine whether the pump assembly is leaking as a function of the signal produced by the air-in-line sensor only if the air trap reservoir initially contains a substantially quantify of air, part of which is forced into the air-in-line sensor if fluid leaks from the pump assembly upstream of the air-in-line sensor when the liquid in the inlet passage is pressurized.

15. In a pump assembly having a plurality of valves, including an inlet valve and an outlet valve, a pumping chamber disposed between the inlet valve and outlet valve, and a control that selectively opens and closes the inlet and outlet valves and activates a driver to pressurize a fluid within the pumping chamber in a pump cycle, apparatus to test for leakage of the pump assembly, comprising:
pressure sensing means for producing a signal indicative of the pressure of fluid in a fluid passage downstream of the outlet valve; and
leak detection means, connected to receive the signal produced by the pressure sensing means, for detecting leakage from the pump assembly as a function of the signal produced by the pressure sensing means immediately after the outlet valve is opened, said outlet valve being opened after fluid within the pumping chamber has been pressurized for an interval of time drain which the driver is inactive to further pressurize fluid in the pumping chamber.

16. The apparatus of claim 15, wherein leakage is detected by the leak detection means if the signal produced by the pressure sensing means indicates that a peak pressure of a pulse propagating through the fluid passage when the outlet valve is opened is less than a predetermined value.

17. The apparatus of claim 15, further comprising means for effecting an alarm when leakage is detected.

18. The apparatus of claim 15, wherein the plurality of valves further include selector valve means for selecting from among a plurality of inlets to the pump assembly a source of fluid for input to the pumping chamber as determined by the control means, said selector valve means being connected in fluid communication with the inlet valve by an inlet passage.

19. The apparatus of claim 18, further comprising an air trap reservoir and air-in-line sensor means, both disposed in the inlet passage, for detecting the presence of air/liquid upstream of the air trap reservoir and producing a signal indicating whether air or liquid is present in the inlet passage at the air-in-line sensor means, wherein the leak detection means are alternatively operative to detect leakage through the selector valve means as a function of the signal produced by the air-in-line sensor means when both the selector valve means and the outlet valve are closed if substantial air is initially present in the air trap reservoir, and if not, to detect leakage through the selector valve means as a function of the signal produced by the pressure sensor means when the outlet valve is opened, releasing pressurized liquid from the pumping chamber, said liquid having been initially trapped between the selector valve means and the outlet valve when initially pressurized.

20. The apparatus of claim 19, wherein the leak detection means determines that the selector valve means are leaking as a function of the signal produced by the air-in-line sensor means if, during pressurization of liquid in the pumping chamber, said air-in-line sensor means begin to indicate the presence of air rather than liquid.

21. In a pump assembly including an inlet valve, an outlet valve, a chamber in which fluid is pressurized during a pump cycle, a pressure sensor disposed downstream of the outlet valve, and a control for selectively initiating the pump cycle, a method for testing the leak proof integrity of the pump assembly, comprising the steps of:
(a) filling the chamber with the fluid;
(b) closing the inlet and the outlet valves;
(c) effecting at least a partial pumping cycle to pressurize fluid in the chamber and then terminating the pumping cycle;
(d) after a predetermined time interval during which the pump assembly is inactive to further pressurize fluid in the chamber, opening the outlet valve; and
(e) monitoring a fluid pressure downstream of the outlet valve, after it is opened and
(f) determining whether the pump assembly has leaked during the predetermined time interval, as a function of said pressure.

22. The method of claim 21, wherein the step of monitoring includes the step of detecting a pressure pulse propagating downstream of the outlet valve after it is opened, and wherein the step of determining whether the pump assembly has leaked includes the step of determining whether a peak of the pressure pulse exceeds a predetermined minimum value, leakage of the fluid from a volume of fluid nominally trapped between the inlet and outlet valved causing the peak to be less than said predetermined value.

23. The method of claim 21, further comprising the step of effecting an alarm if a leak is detected.

24. The method of claim 21, further comprising the step of repeating steps through a plurality of times, wherein step f comprises the step of determining whether the pump assembly is leaking as a function of the pressure in a plurality of such repetitions.

25. A method for testing leakage integrity in a pump cassette including a plurality of valves, comprising the steps of:

(a) filling the pump cassette with a liquid;

(b) closing at least two valves on the pump cassette to define a nominal sealed volume in which liquid is trapped between said valves;

(c) effecting operation of the pump to pressurize the liquid trapped in the nominal sealed volume and thereafter stopping the pump to test for leakage;

(d) waiting an interval of time during which the pump is not operating to further pressurize the liquid trapped in the nominal sealed volume;

(e) opening one of the valves; and (f) detecting that leakage has occurred from the nominal sealed volume defined by the closed valves, as a function of a pressure downstream of said one of the valves after it is opened.

26. The method of claim 25, wherein the step of detecting leakage comprises the step of determining that a pressure pulse of less than a predetermined magnitude propagates downstream of said one valve when it is opened.

27. The method of claim 26, further comprising the step of closing another of the valves after waiting the interval of time and before opening said one valve, to define a smaller volume of trapped liquid.

* * * * *

UNITED STATES PATENT AND TRADEMARK OFFICE
CERTIFICATE OF CORRECTION

PATENT NO. : 5,000,664

DATED : March 19, 1991

INVENTOR(S) : Lawless et al.

It is certified that error appears in the above-identified patent and that said Letters Patent is hereby corrected as shown below:

| Column | Line | |
|---|---|---|
| 1 | 56 | "form" should be --from-- |
| 2 | 53 | "n" should be --in-- |
| 2 | 56 | "liquid" should be --fluid-- |
| 2 | 61 | "filing" should be --filling-- |
| 2 | 63 | "pressure" should be --pressurize-- |
| 3 | 20 | "pressure" should be --pressurize-- |
| 3 | 21 | "form" should be --from-- |
| 4 | 51 | After the words "outlet valve" insert the number --56-- |
| 5 | 13 | "without" should be --within-- |
| 5 | 38 | After the word "fluid" insert the word --flow-- |
| 5 | 39 | "servers" should be --serves-- |
| 7 | 33 | "form" should be --from-- |
| 7 | 48 | "drier 10" should be --driver 150-- |
| 8 | 9 | "block 240" should be --block 204-- |
| 8 | 21 | "mater" should be --matter-- |
| 8 | 53 | "FIGS:9A-9C" should be --FIGURES 9A-9C-- |
| 8 | 57 | "flowcharts" should be --flow charts-- |
| 9 | 18 | "pints" should be --points-- |
| 9 | 26 | "Implemented" should be --implemented-- |
| 9 | 47 | "IN" should be --In-- |

UNITED STATES PATENT AND TRADEMARK OFFICE
CERTIFICATE OF CORRECTION

PATENT NO. : 5,000,664

DATED : March 19, 1991

INVENTOR(S) : Lawless et al.

It is certified that error appears in the above-identified patent and that said Letters Patent is hereby corrected as shown below:

| Column | Line | |
|---|---|---|
| 9 | 54 | "ragging" should be --ranging-- |
| 10 | 31 | "fi" should be --if-- |
| 10 | 54 | "determine" should be --determines-- |
| 10 | 55 | "Air Trp" should be --Air__Trp-- |
| 10 | 55, 56 | "Air Trg" should be --Air__Trg-- |
| 10 | 60 | "Air$_{13}$Trp" should be --Air__Trp-- |
| 10 | 63 | "push back" should be --pushback-- |
| 11 | 1 | "push back" should be --pushback-- |
| 11 | 15 | After the word "liquid" insert the words --is present-- |
| 11 | 17 | "push back" should be --pushback-- |
| 12 | 42 | "valve 55" should be --valve 56-- |
| 13 | 10 | After the words "test, in" insert the word --a-- |
| 13 | 20 | "an" should be --and-- |
| 14 | 63 | After the word "passage" insert the words --from the pressure-- |
| 15 | 17 | After the word "air" insert the word --trap-- |
| 15 | 44 | "substantially" should be --substantial-- |
| 15 | 44 | "quantify" should be --quantity-- |

UNITED STATES PATENT AND TRADEMARK OFFICE
CERTIFICATE OF CORRECTION

PATENT NO. : 5,000,664
DATED : March 19, 1991
INVENTOR(S) : Lawless et al.

It is certified that error appears in the above-identified patent and that said Letters Patent is hereby corrected as shown below:

| Column | Line | |
|---|---|---|
| 15 | 67 | "drain" should be --during-- |
| 16 | 44, 45 | "leak proof" should be --leakproof-- |
| 16 | 55 | After the word "valve" delete the word "and" |
| 16 | 57 | "opened" should be --opened;-- |
| 17 | 1 | "valved" should be --valves-- |
| 17 | 6 | "steps through a plurality" should be --steps a through e a plurality-- |

Signed and Sealed this

Fourteenth Day of June, 1994

*Attest:*

BRUCE LEHMAN

*Attesting Officer*     *Commissioner of Patents and Trademarks*